United States Patent [19]

Markovits et al.

[11] 4,011,350
[45] Mar. 8, 1977

[54] METHOD OF MAKING MICROSCOPE SLIDE SYSTEM

[75] Inventors: Arthus L. Markovits, Millburn; Stanley W. Wolfson, West Orange, both of N.J.

[73] Assignee: Clinical Sciences, Inc., Whippany, N.J.

[22] Filed: May 29, 1973

[21] Appl. No.: 364,240

Related U.S. Application Data

[62] Division of Ser. No. 140,497, May 5, 1971, Pat. No. 3,736,042.

[52] U.S. Cl. .................................. 427/2; 424/12; 427/287
[51] Int. Cl.$^2$ ........................................ G02B 21/34
[58] Field of Search .......... 206/223, 229, 370, 456, 206/523, 803; 350/95; 427/2, 287, 385; 428/210; 23/253 R, 253 TP

[56] References Cited

UNITED STATES PATENTS

| 2,090,914 | 8/1937 | Porter | 350/95 |
|---|---|---|---|
| 3,139,352 | 6/1964 | Coyner | 427/287 |
| 3,666,421 | 5/1972 | Price | 23/253 TP |

FOREIGN PATENTS OR APPLICATIONS

| 419,339 | 1/1934 | United Kingdom | 350/95 |
|---|---|---|---|
| 1,104,627 | 8/1965 | United Kingdom | 350/95 |

*Primary Examiner*—Ronald H. Smith
*Assistant Examiner*—S. Silverberg

[57] ABSTRACT

A microscope slide assembly and a method of preparing such which includes an optically clear glass slide having a controlled thickness fluorocarbon layer coated on one planar surface. The layer is provided with a multiplicity of openings to form wells on the glass slide. An agar solution may be incorporated within the wells to provide an adhesive layer. In addition, a particular antigen may be layered on top of the agar composition to provide a completed assembly wherein only a patient's serum is needed to process a microscopic examination. For use in fluorescent microscopy, a film body grade Teflon containing an adhesive is used to provide the uniform fluorocarbon layer. The microscopic assembly may be enclosed within an environment isolation container to prevent contamination of the assembly from the ambient surroundings when the antigen is combined with the agar solution.

9 Claims, 4 Drawing Figures

U.S. Patent   Mar. 8, 1977   4,011,350
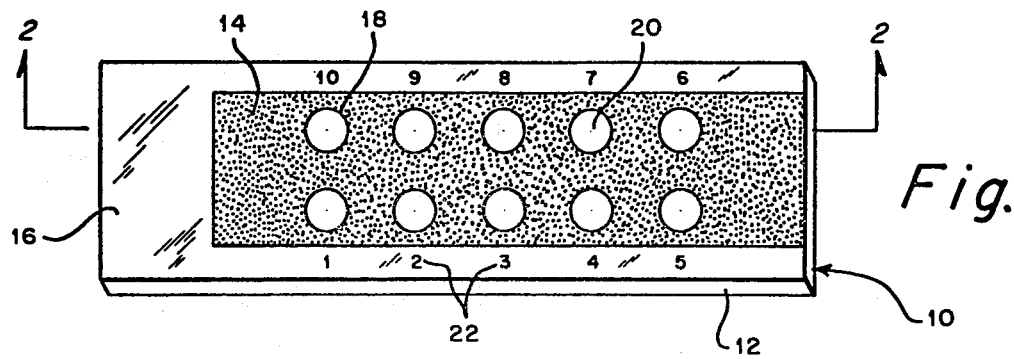
Fig. 1
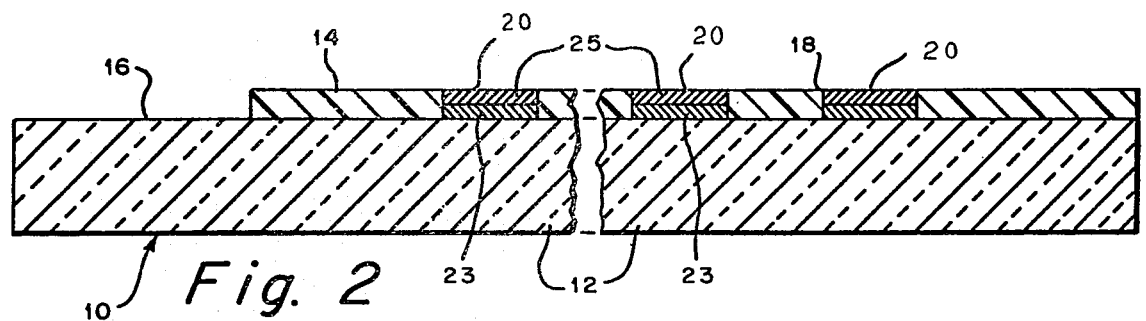
Fig. 2
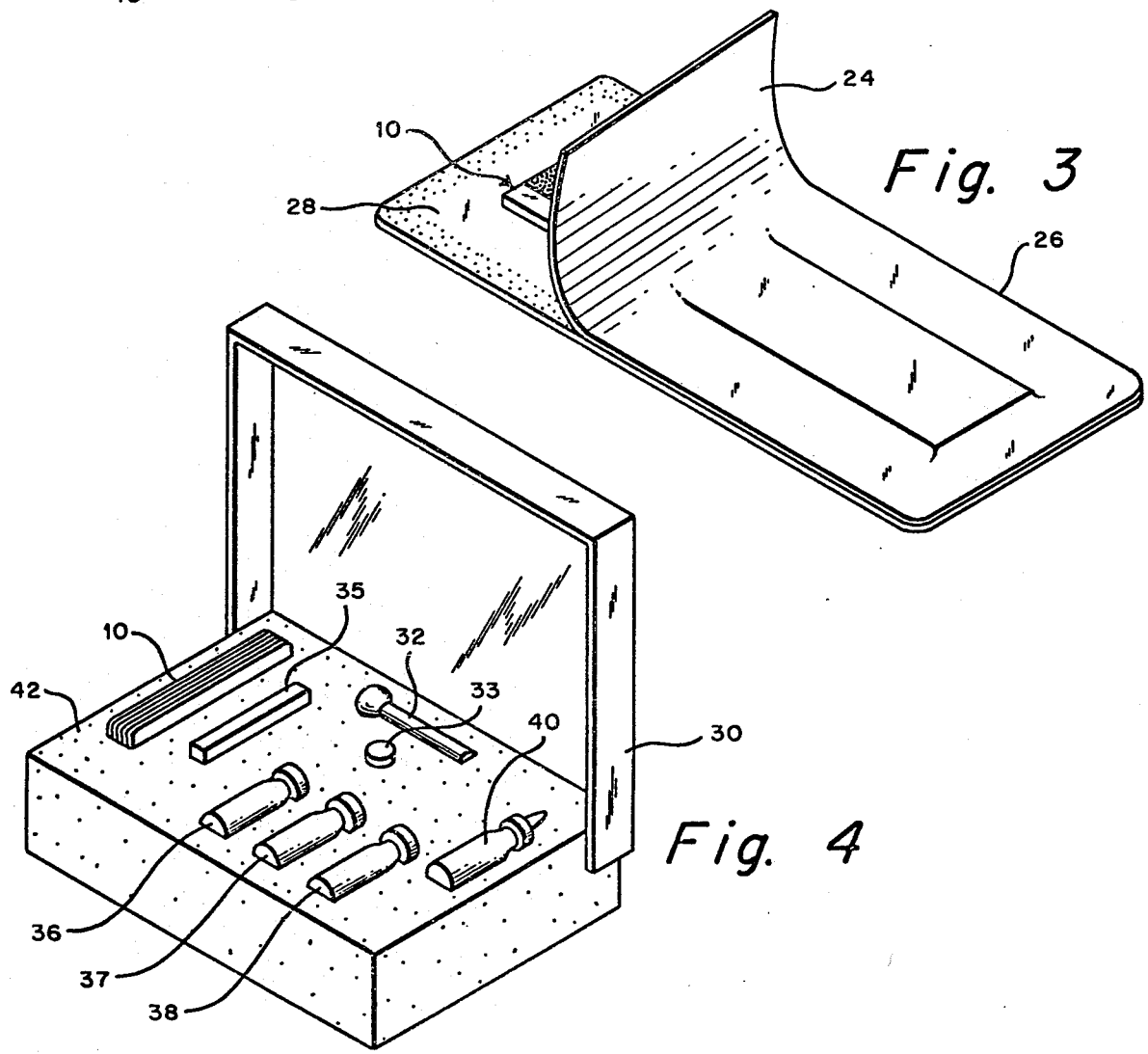
Fig. 3
Fig. 4

METHOD OF MAKING MICROSCOPE SLIDE SYSTEM

This is a division, of application Ser. No. 140,497, filed May 5, 1971 now U.S. Pat. No. 3,736,042.

BACKGROUND OF THE INVENTION

1. Field of the Invention

This invention pertains to the field of microscope slides. In particular this invention relates to microscopic slide assemblies used in fluorescent microscopy methods. More in particular, this invention pertains to the forming of reactant regions within a predetermined thickness layer of a fluorocarbon composition on the surface of a glass slide to permit a microscopic examination. Of further importance, this invention relates to the inclusion of agar and specific antigens within the wells formed within the fluorocarbon layer masking the glass slide.

2. Prior Art

Microscope slides are well known in the art. However, the field of fluorescent microscopy has been seriously hampered due to the fact that microscopic slides could not be produced having a series of reactant regions formed within a coating layer. In prior microscope assembly slides, the coating layers were too thick to permit accurate focusing of the microscope during examination. Prior slide coatings using ceramics have been tried, but such presents a thickness which is unacceptable and in many cases does not allow the micropodist to focus on the specimen without cracking the cover slip. Additionally, a wide variety of paints have been tried as a coating agent, however, such paints do not provide sufficient surface tension characteristics to prevent a specimen drop from running out and thereby possibly contaminating an adjacent well.

Present direct fluorescent serology systems require the scientist or technician to isolate a particular etiologic agent in pure culture before an identification can be made. This requirement forces a test delay between 24 and 96 hours, and in some cases the isolation may not be accomplished within the laboratory. In contrast, the present invention provides pure cultures of antigens for use in the slide assembly and ready for immediate use in a indirect fluorescent test.

Present systems utilized in fluorescent microscopy do not provide the combination of an agar adhesive layer and a specific antigen positioned within a plurality of openings in the masking layer. Thus, forcing additional steps to be taken by the operator in carrying out the appropriate microscopic examination.

Additionally, present commercial conjugated reagents are prepared in 1 to 5 ml. amounts and require a pre-use titer evaluation to determine the working dilution to be used. Large quantities of this nature require storage and handling time loss.

Utilization of a masked fluorocarbon layer having a critical thickness range between $7.5 \times 10^{-5}$ and $1.5 \times 10^{-4}$ inch which is deposited on a microscope slide surface has not been found by the inventor. Of further importance, the prior art has not suggested the use of a 0.02% agarose aqueous solution for inclusion into openings of the fluorocarbon layer defining an adhesive layer. There is also no mention of inserting a specific antigen layer on top of the agarose layer to form a microscope slide assembly which is self-contained and only lacking the patient's sera.

SUMMARY OF THE INVENTION

An object of the present invention is to provide a microscope slide system suitable to be used in the field of fluorescent microscopy.

Another object of the present invention is to provide an optically clear microscope slide having a predetermined thickness layer to effect a multiplicity of individual uniform self-contained reactant areas.

A still further object of the present invention is to provide a masking layer composition for a microscope slide such that the total slide thickness allows for focusing of a microscope while at the same time having surface tension properties sufficient to prevent a specimen from running out and contaminating another reactant area.

Another object of this invention is to provide a complete microscope slide system where reactant areas are coated with an adhesive layer and a particular antigen.

Another object of this invention is to provide a microscope slide system including an agar layer in combination with a specific antigen packaged within a container isolated from the external atmosphere and having its own predetermined environment.

A microscope slide system for singularly determining a plurality of reactions. A glass slide being optically clear defines a planar contour dimension with opposing boundary surfaces. A fluorocarbon layer is deposited on one of the boundary surfaces. The layer includes a plurality of openings passing therethrough for forming reactant regions on the boundary surface of the glass slide. The thickness of the fluorocarbon layer approximates the range $7.5 \times 10^{-5}$ to $1.5 \times 10^{-4}$ inch.

BRIEF DESCRIPTION OF THE DRAWINGS

FIG. 1 is a perspective view of the microscope slide assembly showing the fluorocarbon masking layer with a plurality of reactant regions;

FIG. 2 is an elevational sectional view of the microscope slide assembly showing the agar and antigen layers located within the reactant regions taken along the section line 2—2 of FIG. 1;

FIG. 3 is a perspective view of the microscope slide assembly within an environment isolating container for use when agar and particular antigens are positioned within the reactant regions; and, FIG. 4 is a perspective view of a microscope slide kit including a set of slide assemblies and an antigen dispenser within a portable container.

DESCRIPTION OF THE PREFERRED EMBODIMENTS

Referring now to FIG. 1, there is shown a microscopic or glass slide system 10 for general use in clinical diagnostic procedures and having a particular application in the field of fluorescent microscopy. System 10 includes optically clear glass slide 12 of thickness between 0.96 and 1.06 mm. having a predetermined or controlled thickness fluorocarbon layer 14 coated on upper surface 16 of slide 12. Layer 14 is provided with a plurality of openings 18 forming wells or reactant regions 20 on upper surface 16. Wells 20 may be open to the ambient environment, include a coating of agar or, in combination, an agar plus specific antigen composition as will be described in detail in following paragraphs.

Fluorescent microscopy is similar in methodology to the compound light microscope processes but is positioned for excitation light in the ultraviolet range, and transmitted light in the visible region, to a particular specimen located in reactant regions 20 of system 10.

A brief description of some of the instrumentation used in fluorescent microscopy, although not part of the inventive concept, will be herein outlined to serve as an aid in the understanding of system 10. The image seen through the working microscope fluoresces brightly and has positive contrast with respect to the surroundings. Where there is a weak fluorescence of the specimen under consideration, monocular microscopes are usually used in a darkened environment surrounding. Binocular microscopes may be used in light surroundings when the fluorescence is intense. Coatings are used on the air-glass surfaces of the microscope to decrease the losses in light transmission that may occur. In general, any non-fluorescing objective may be used, however, an 8mm and 20× ocular is often used in combination. Objectives having fluorite elements as well as chromatic condensers are not usually used since such may produce a glare from autofluorescence of any cemented surfaces. In some cases, operators prefer dark-field methods using a bispheric, or paraboloidally shaped condenser instead of a bright-field condenser.

Absorbing filters are sometimes, but not always, located in the microscope between the operator's eye and the objective, which removes any other exciting radiation not absorbed by the specimen on system 10. The filter itself may be of different forms, complementary to the radiation used or absorbing only the ultraviolet region when the specimen is to be observed in natural colors.

Darkfield immunofluorescence microscopy is utilized in a series of microbiological systems. Application of this technique permits visualization of specific antigen antibody reactions on the cellular level. Such a method offers the applied scientist a means for locating pathogenic microorganisms and a method of indirectly detecting the infection of man and animals with pathogenic microorganisms.

Fluorescent microscopy utilizes oblique lighting as opposed to a direct lighting system normally experienced in the standard or white light microscopy analysis. The illumination is directed on the lower surface of slide system 10 with the microscope adjacent wells 20 on upper surface 16. The light source is generally a high intensity mercury vapor or halogen type bulb being projected through a series of filters permitting only the ultraviolet band of light to penetrate the microscope.

Reagents combined with a fluorescent dye or a dye capable of being excited by ultraviolet light are placed within reactant regions or wells 20. When the above described illumination is directed through reactant regions 20 the combined composition emits a fluorescent illumination. The focusing requirements for a microscope under this type of illumination is critical for technique success. The operator must adjust the microscope to a point almost touching the cover slip (not shown) which is placed on upper surface 16 of system 10. Therefore, the thickness of system 10 must be controlled precisely, otherwise one cannot focus the microscope in a manner to bring the particular organism under inspection into an acceptable range without cracking the cover slip and/or damaging the microscope in some way.

In final form, system 10 may take on one of three possible combinations. A first combination includes glass slide 12 with predetermined fluorocarbon layer 14 masking upper surface 16. In this presentation openings or singularities 20 are formed through layer 14 to provide wells or reactant regions 20. However, the base surface of regions 20 are upper surface 16 open to the external environment. In a second presentation, an adhesive layer of agar is applied to reactant regions 20 within the masked portion of slide 12. This type of treatment allows a large number of organisms to be retained on each reactant surface 20 during a microscopic examination. A third preparation of system 10 includes masked slide 12 containing the mastic or agar layer in combination with a particular antigen. In this combination, as shown in FIG. 2, agar layer 23 is incorporated within reactant region 20 and abated with a specific antigen layer 25 as shown. Agar layer 23 serves as an adhesive in this case to hold antigen layer 25 within regions 20 during examination. Such antigens may include, but not be limited to rickettsia, virus infected tissue cultures, fungi, parasites, and special vectors coated with antigens such as toxins, allergens, etc.

Fluorocarbon layer 14 is of prime importance in the construction of system 10. In composition, layer 14 presents the type of surface tension variation between reactant regions 20 and surrounding layer 14 to prevent the drops of liquid placed in wells 20 from running out. In this manner, many different reagents which are required to perform a series of test reactions may be applied to areas 20 without danger of any cross contamination causing invalidation of test results. In addition, layer 14 must be as thin as possible in order that after placement of a cover slip over system 10, the overall thickness of the assembly is small enough so that the microscope may still be focused as has been previously described.

In summary of layer 14 it is then noted that it must include the properties of being applied in a thin coat but have sufficient surface tension properties to maintain a specimen within wells 20. Empirical testing has shown that a glass bonding grade of Teflon may effectively be used for coated layer 14. In particular, "Fluoroglide" produced by Chemplast Inc. has been used successfully as the masking agent for system 10. This composition is a fluorocarbon product Teflon of film body grade including an adhesive to allow securement of layer 14 to upper surface 16. In its most advantageous use, layer 14 should consist of a single layer of Teflon particles sufficient to cover surface 16 in a contiguous, uniform layer. The thickness of layer 14 has been found to be useful between the ranges of $7.5 \times 10^{-5}$ to $1.5 \times 10^{-4}$ inches with an optimized thickness substantially equal to $1.0 \times 10^{-4}$ inch.

Masking of glass slide 12 is accomplished by spraying fluorocarbon or Teflon layer 14 onto upper surface 16 under pressure. A template is placed over surface 16 and an automated unit, not important to the inventive concept herein defined, sprays layer 14 onto slide 12 to form system 10 in accordance with the parameters already described in the previous discussion.

Wells or reactant regions 20 may include adhesive layer 23 contiguous to upper surface 16 of slide 12 to present an adhering surface within region 20. Layer 23 causes the organisms of the antigen to adhere when the antigen dries on the surface of this mastic. Adhesive layer 23 prevents the organisms from being washed off system 10 in the normal processing procedure prior to microscopic examination. Empirical experimentation has shown that agar layer 23 composed of 0.01 to 0.05% agarose aqueous solution has performed with a high degree of success. Optimum results have been found when layer 23 is composed of a 0.02% agarose aqueous solution and uniformly deposited within region 20 on upper surface 16. In addition, other high purity inert agar preparations have been used in forming adhesive layer 23, such as special noble agar and ionagar. The result of including layer 23 in system 10 permits usage of such by the scientist with less effort than if layer 23 had to be applied at the time of the examination.

Antigen layer 25 may be incorporated onto agar layer 23 to provide system 10 as a complete assembly for the testing procedure with the only unknown quantity added being the patient's sera. The sera, in this case is placed within wells 20, then appropriate reagent is added to each well 20 and after additional washing the cover slip is positioned over system 10. A direct microscopic examination is then made to determine whether the patient response is positive or negative.

Coupling of antibodies to a fluorescent dye may be accomplished by chemical reactions which do not disturb the particular reactivity of an antibody with an antigen. A fluorescent dye which is commonly used in the field of fluorescent microscopy is fluorescein isophiocyanate. The antibodies conjugated by fluorescent dyes are in most cases called fluorescent antibodies and are used as stains for the detection of antigens in cells and tissues. The fluorescent antibody is often deposited from solution on tissue section or particular cell preparation, and these regions are viewed in a characteristic color when viewed under a fluorescence microscope.

As shown in FIG. 1, each reactant area is indexed in accordance with a prearranged set of numerals 22 to identify particular reactant regions within layer 14. Numerals 22 may be formed of the same fluorocarbon layer composition by incorporating these indices within the same masking template as that used in the spraying of layer 14. In like manner, numerals 22 may be etched into glass slide 12 upper surface 16 or some like method not important to the inventive concept herein detailed.

The method of making microscope slide system 10 includes as a first step the depositing of a layer of fluorocarbon 14 on upper surface 16 of optically clear glass slide 12. A standard microscope slide 12 may be used having a thickness with the range between 0.96 and 1.06 mm. Depositing layer 14 on surface 16 is accomplished by masking slide 12 with a template or like devise to provide a plurality of openings 18 for forming reactant regions 20 within layer 14 and spraying layer 14 onto surface 16. The layer thickness may be within the range of $7.5 \times 10^{-5}$ to $1.5 \times 10^{-4}$ inch. After layer 14 is deposited, a 0.01 to 0.05% aqueous agarose solution is applied to reactant regions 20 to form layer 23 which is shown in FIG. 2.

The step of applying the aqueous agarose solution is initiated by mixing a predetermined quantity of agarose with a known amount of distilled water at ambient temperature conditions. This procedure forms an aqueous agarose suspension which is permitted to stand at room temperature for a time approximating one-quarter of an hour. The suspension which is contained within a flask is then warmed by immersing the flask into boiling water. The suspension is warmed to a temperature approximately equal to 100° C. wherein the agarose dissolves and forms an agarose aqueous solution.

The warmed agarose solution is then tempered from an initially warm phase of 100° C. to an application phase within the temperature range of 55° – 60° C. A predetermined quantity of the agarose solution is then inserted within reactant regions 20 of slide 12 to form adhesive layer 23. In general, one one hundred twentieth of a mm. of argose solution is inserted into each of the regions 20. During this operation, slide 12 is maintained within a sterile hood having sterile circulating warm air and is positioned on a platform which is heated to a temperature of approximately 80° C. A sterilized atmosphere is maintained under the hood in order to remove any dust particles or other debris that may stick to slide 12. The final step is drying the agarose solution within regions 20 to form layer 23. Care must be taken to insure uniform drying of the solution, therefore, contiguous contact of the agarose solution around the periphery of wells 20 must be achieved prior to the drying step. It is preferred that the drying time not exceed 1½ minutes to avoid concentric rings from forming at the surface of layer 23.

Antigen layer 25 may be added onto layer 23 within regions 20 to permit a completed system 10 wherein only the patient's sera need be added for a complete examination. As an initial step in adding antigen to layer 23 surface proteins and other interfering debris are removed from the antigen in accordance with known procedures in this art. The antigen being held in suspension is then adjusted in a buffering solution to provide a proper concentration of cells. In general, adjustment is made so that one lambda drop of the cell suspension contains 15–30 observable cells within each of wells 20. A standard microscopic magnification of 400× or 1000× is commonly used for these tests.

A one lambda volume of each antigen is inserted into each region 20 on top of layer 23. The antigen is uniformly spread over layer 23 contacting fluorocarbon layer 14 walls of regions 20 thus permitting optimized drying time for antigen layer 25. The drying is accomplished under ambient temperature conditions within a sterile hood. Upon completion of the drying step slide 12 is placed in an appropriate fixature such as alcohol or acetone or some like composition. Slide 12 may then be dried and placed in a hermetically sealed envelope for storage purposes.

An embodiment of the invention is shown in FIG. 3 where microscope slide system 10 is enclosed within envelope or container 24. Edges or boundary 26 are sealed to prevent contamination of system 10 with the external environment. Composition of container 24 may be of aluminum foil, plastic film or some like material capable of hermetically sealing system 10 from the ambient atmosphere before use. In general, the structural characteristics of container 24 may provide either a rigid or pliable restraint. Additionally, desicant 28 may be formed on an inner surface of envelope 24 to promote a moisture free environment for system 10 when stored. Where agar and a particular antigen are incorporated in combination into wells or reactant regions 20 an inert internal environment may be provided by filling the interior of envelope 24 with an inert gas such as nitrogen or some like element before the sealing of edge 26 to prevent contamination. In this manner, system 10 containing both the adhesive layer and specific antigen may be stored for long periods of time without prospects of contamination of system 10.

Another embodiment of the present invention is shown in FIG. 4 where microscope slide system 10 is presented in a prepackaged kit form mounted within container 30 and in simplest form being constructed of plastic, cardboard or some like material. System 10 is included in combination with cartridge member 32 which contains an antigen or antibodies for insertion into regions 20. Cartridge member 32 contains a pretitered conjugate reagent presenting a pretested, lyophilized aliquot of the conjugate reagent. Also included in the kit is the dispensing head or needle 33 in an encompassing plastic container. Both cartridge member 32 and dispensing head 33 are similar in construction to the cartridge dispensing means disclosed in U.S. Pat. No. 3,426,811.

Additionally container 30 may preferably be provided with a plurality of cover slips 35 each of which having a standard thickness approximating 0.17 mm. as well as varying strength control reagents 36, 37, and 38 corresponding generally to strongly positive, weakly positive and negative reagents. The kit also contains a properly buffered microscope mounting media 40 to provide a compact all inclusive assembly for use by the scientist in the microscopic examination. All of the elements thus associated with the kit may be mounted within inserts provided within plastic molded platform 42 which comprises a portion of container 30.

In final general discussion, infectious agents such as viruses, bacteria and antigenic materials are inanimate and formed basically of a protein base. When such agents gain entrance to the body, substances or antibodies are produced which react with these alien or extraneous agents. The antibody production is elicited by the antigens. When antibodies in a solution are contacted with a soluble antigen, a precipitate is formed and particles stick together in an adhesive fashion. During this combination of interaction of molecules, specificity occurs.

In the scope of the work undertaken with or envisioned in the field of fluorescent microscopy, the invention as has been detailed herein provides a low cost, easily maintainable and highly efficient means for increasing the applicability of the entire area in the field of clinical diagnostic techniques. A number of modifications and variations of the present invention as hereinbefore set forth may be made without department from the spirit and skill thereof, and therefore only such limitations should be imposed as are indicated in the appended claims.

We claim:
1. A method of preparing a microscope slide system including the steps of:
   a. spraying a layer of fluorocarbon on one surface of a microscope slide, said layer having an approximate thickness range between $7.5 \times 10^{-5}$ and $1.5 \times 10^{-4}$ inch, said fluorocarbon layer having a plurality of openings passing therethrough for forming reactant regions on said surface of said microscope slide; and,
   b. applying a layer of 0.02% agarose solution to said surface of said microscope slide only within and completely covering said reactant region.

2. The method of preparing a microscope slide system as recited in claim 1 wherein the step of applying said layer of agarose includes the steps of:
   a. forming an agarose solution with distilled water;
   b. maintaining said agarose solution within a temperature range of approximately 55° to 60° C;
   c. inserting a predetermined quantity of solution within said reactant regions of said microscope slide; and,
   d. drying said agarose solution within said reactant regions.

3. The method of preparing a microscopic slide system as recited in claim 2 wherein the step of forming an agarose solution includes the steps of:
   a. mixing a predetermined quantity of agarose with a predetermined amount of distilled water within a flask to form an agarose suspension;
   b. warming said suspension to a temperature approximating 100° C. to form an agarose solution; and
   c. tempering said warmed agarose solution until a temperature between 55° and 60° C. is reached.

4. The method of preparing a microscopic slide system as recited in claim 3 wherein the step of warming said agarose suspension includes the step of placing said suspension containing flask into boiling water until said suspension forms a solution.

5. The method of preparing a microscope slide system as recited in claim 2 wherein the step of inserting said agarose solution into said reactant regions includes the step of dropping one one hundred twentieth mm. of agarose solution into each of said reactant regions.

6. The method of preparing a microscope slide system as recited in claim 1 including the additional step of adding a predetermined quantity of a specific antigen within said reactant regions after application of said agarose solution.

7. The method of preparing a microscope slide system as recited in claim 6 wherein the step of adding antigen includes the steps of:
   a. removing surface proteins and other interfering debris from said antigen;
   b. adjusting said antigen in buffering solution to provide a predetermined concentration of antigen cells;
   c. inserting said antigen into said reactant regions in a substantially uniform thickness layer; and,
   d. placing said antigen coated slide into a fixative for a predetermined length of time.

8. The method of preparing a microscope slide system as recited in claim 7 wherein the step of adjusting said antigen includes the step of establishing a concentration of 15 to 30 observable antigen cells within each of said reactant regions of said slide.

9. The method of preparing a microscope slide system as recited in claim 8 wherein the step of inserting said antigen includes the steps of:
   a. placing a one lambda volume of each of said antigens into each of said reactant regions; and,
   b. drying said layer of antigens placed within said reactant regions, said antigen layers being contiguous with said 0.02% solution of dried agarose.

* * * * *